United States Patent
Okuzumi

(10) Patent No.: US 6,587,734 B2
(45) Date of Patent: *Jul. 1, 2003

(54) CARDIO THERAPEUTIC HEART SACK

(75) Inventor: Yuzi Okuzumi, Parker, CO (US)

(73) Assignee: Acorn Cardiovascular, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/431,605

(22) Filed: Nov. 1, 1999

(65) Prior Publication Data

US 2002/0173824 A1 Nov. 21, 2002

Related U.S. Application Data

(60) Provisional application No. 60/106,960, filed on Nov. 4, 1998.

(51) Int. Cl.[7] .................................................. A61N 1/05
(52) U.S. Cl. ........................................ 607/129; 600/16
(58) Field of Search ............................ 607/2, 119–132; 600/373–375, 16

(56) References Cited

U.S. PATENT DOCUMENTS 3,587,567 A     6/1971  Schiff (List continued on next page.)

FOREIGN PATENT DOCUMENTS

| DE | 295 17 393 U1 | 3/1996 |
|---|---|---|
| EP | 0 280 564 | 8/1988 |
| EP | 0 303 719 | 2/1989 |
| JP | 60203250 | 10/1985 |
| JP | 01-145066 | 6/1989 |
| SU | 1009457 A | 4/1983 |
| WO | WO 98/29041 | 7/1998 |
| WO | WO 98/58598 | 12/1998 |

OTHER PUBLICATIONS

Capouya, et al., "Girdling Effect of Nonstimulated Cardiomayoplasty on Left Ventricular Function," The Society of Thoracic Surgeons, 56:867–871 (1993).

Cohn, "The Management of Chronic Heart Failure", The New Eng. J. of Med., 335 (7): 490–498 (Aug. 15, 1996).

(List continued on next page.)

Primary Examiner—Jeffrey R. Jastrzab
(74) Attorney, Agent, or Firm—Merchant & Gould P.C.

(57) ABSTRACT

This invention relates to implantable heart sack that can be equipped with pacemaker leads and/or defibrillation leads for the treatment of cardiomyopathy, hypertrophic cardiomyopathy, tachycardia, bradycardia, ventricular fibrillation, atrial fibrillation etc. The heart sack was prepared from biocompatible, biostable, implantable polyetherurethane, polycarbonateurethane, silicone, polysiloxaneurethane, polyfluoroethylene, or hydrogenated poly(styrene-butadiene) copolymer. The heart sack is equipped with attached sutures to make it easier to attach onto the heart. The heart sack can be made semipermeable or perforated to have numerous holes. The heart sack can be reinforced with fiber or filament. Ordinary pacemaker leads can be attached to the inner side of the heart sack. However, the pacemaker leads of this invention were prepared from noble metal (gold, platinum, rhodium and platinum-Rhodium alloys) or stainless steel coated, deposited or plated mono-filaments, yarns, braids, cords, wires or films, or cylindrical tubes of polyamide, polyimide, polyester, and/or polypropylene that are encased in multi-lumen insulating tube or coaxial tube made of biocompatible, biostable, implantable polyetherurethane, polycarbonateurethane, silicone, polysiloxaneurethane, polyfluoroethylene, or hydrogenated poly(styrene-butadiene) copolymer. The leads can be mounted onto the inner surface of the heart sack and contoured to the heart. The heart sack can be coated with hydrophilic coating containing an antimicrobial agent that gives the heart sack a low coefficient of friction, excellent biocompatibility and antimicrobial properties.

20 Claims, 2 Drawing Sheets

U.S. PATENT DOCUMENTS

| | | |
|---|---|---|
| 3,983,863 A | 10/1976 | Janke et al. |
| 4,048,990 A | 9/1977 | Goetz |
| 4,403,604 A | 9/1983 | Wilkinson et al. |
| 4,428,375 A | 1/1984 | Ellman |
| 4,630,597 A | 12/1986 | Kantrowitz et al. |
| 4,690,134 A | 9/1987 | Snyders |
| 4,821,723 A | 4/1989 | Baker, Jr. et al. |
| 4,827,932 A | 5/1989 | Ideker et al. |
| 4,878,890 A | 11/1989 | Bilweis |
| 4,936,857 A | 6/1990 | Kulik |
| 4,957,477 A | 9/1990 | Lundback |
| 4,973,300 A | 11/1990 | Wright |
| 4,976,730 A | 12/1990 | Kwan-Gett |
| 5,057,117 A | 10/1991 | Atweh |
| 5,087,243 A | 2/1992 | Avitall |
| 5,131,905 A | 7/1992 | Grooters |
| 5,150,706 A | 9/1992 | Cox et al. |
| 5,186,711 A | 2/1993 | Epstein |
| 5,192,314 A | 3/1993 | Daskalakis |
| 5,256,132 A | 10/1993 | Snyders |
| 5,290,217 A | 3/1994 | Campos |
| 5,356,432 A | 10/1994 | Rutkow et al. |
| 5,383,840 A | 1/1995 | Heilman et al. |
| 5,385,156 A | 1/1995 | Oliva |
| 5,429,584 A | 7/1995 | Chiu |
| 5,507,779 A | 4/1996 | Altman |
| 5,524,633 A | 6/1996 | Heaven et al. |
| 5,603,337 A | 2/1997 | Jarvik |
| 5,647,380 A | 7/1997 | Campbell et al. |
| 5,702,343 A | 12/1997 | Alferness |
| 5,713,954 A | 2/1998 | Rosenberg et al. |
| 5,800,334 A | 9/1998 | Wilk |
| 5,800,528 A | 9/1998 | Lederman et al. |
| 5,824,028 A | 10/1998 | Knisley |
| 6,076,013 A * | 6/2000 | Brennan et al. ............... 607/2 |
| 6,077,214 A | 6/2000 | Mortier et al. |
| 6,077,218 A | 6/2000 | Alferness |
| 6,085,754 A | 7/2000 | Alferness et al. |
| 6,123,662 A | 9/2000 | Alferness et al. |

OTHER PUBLICATIONS

Kass et al., "Reverse Remodeling From Cardiomyoplasty in Human Heart Failure, External Constraint Versus Active Assist", Circulation 91 (9): 2314–2318 (May 1, 1995).

Levin et al., "Reversal of Chronic Ventricular Dilation in Patients With End–Stage Cardiomyopathy by Prolonged Mechanical Unloading", Circulation 91 (11): 2717–2720 (Jun. 1, 1995).

Oh et al., "The Effects of Prosthetic Cardiac Binding and Adynamic Cardiomyoplasty in a Model of Dilated Cardiomyopathy," J. Thorac. Cardiovasc. Surg., 116:148–153 (1998).

Revista Espanola de Cardiologia, vol. 51, No. 7 (Abstract in English)(Jul. 1998).

Vaynblat, M. et al., "Cardiac Binding in Experimental Heart Failure," Abstract in Supplement to Circulation 92(8):1810 (Oct. 15, 1995).

Vaynblat, M. et al., "Cardiac Binding in Experimental Heart Failure," Ann. Thorac. Surg., 64:81–85 (1997).

* cited by examiner

FIG.1 HEART & BLOOD VESSELS
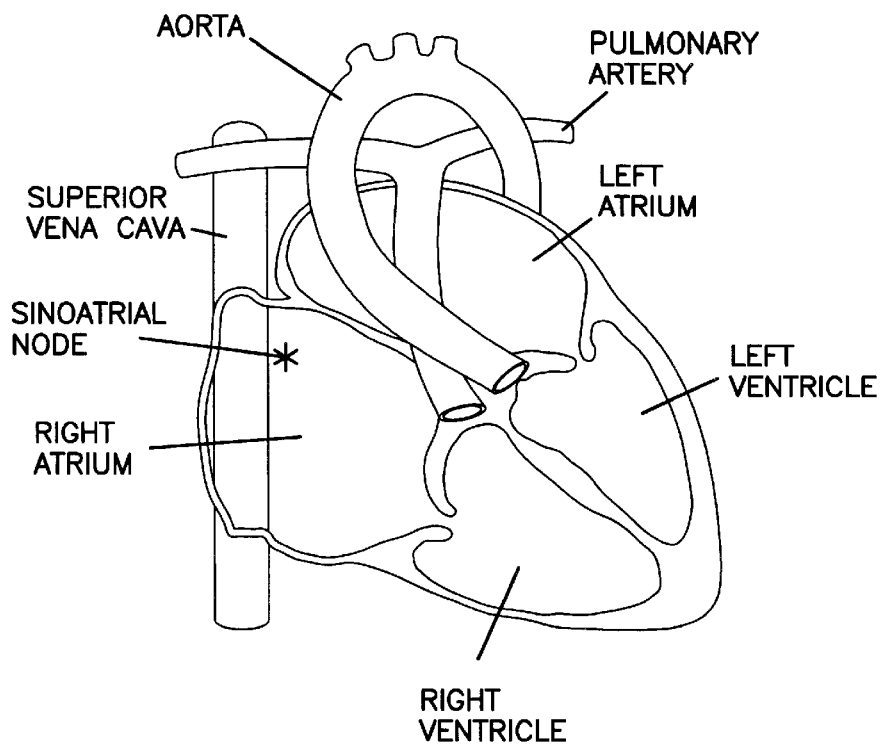
FIG.2 HEART SACK
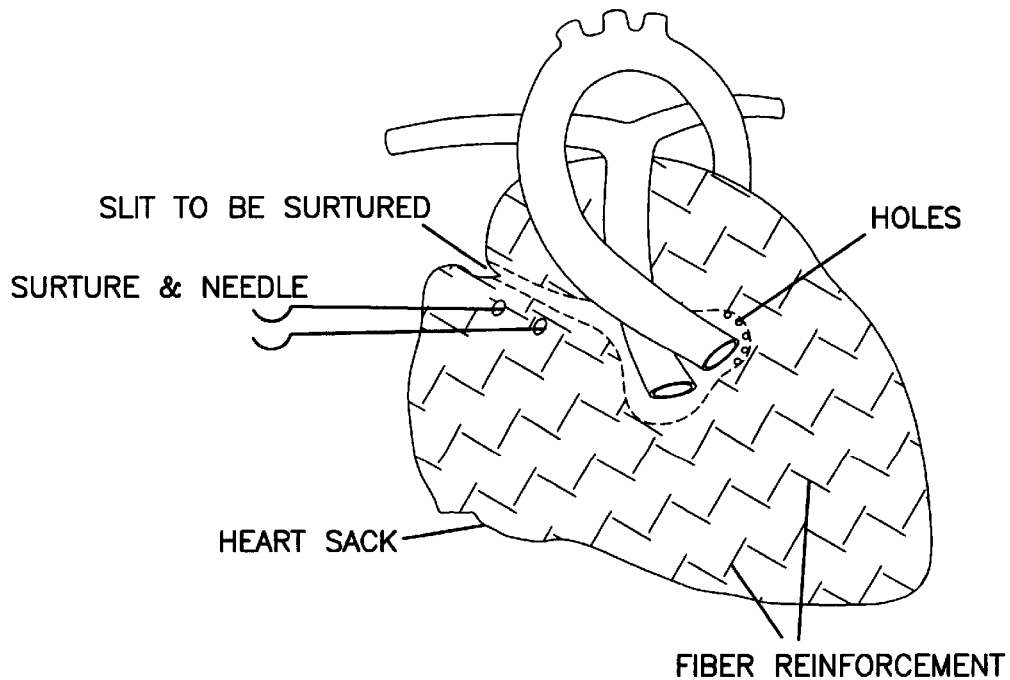

FIG.3 PLATINUM COATED FIBER AND FILM ELECTRODES
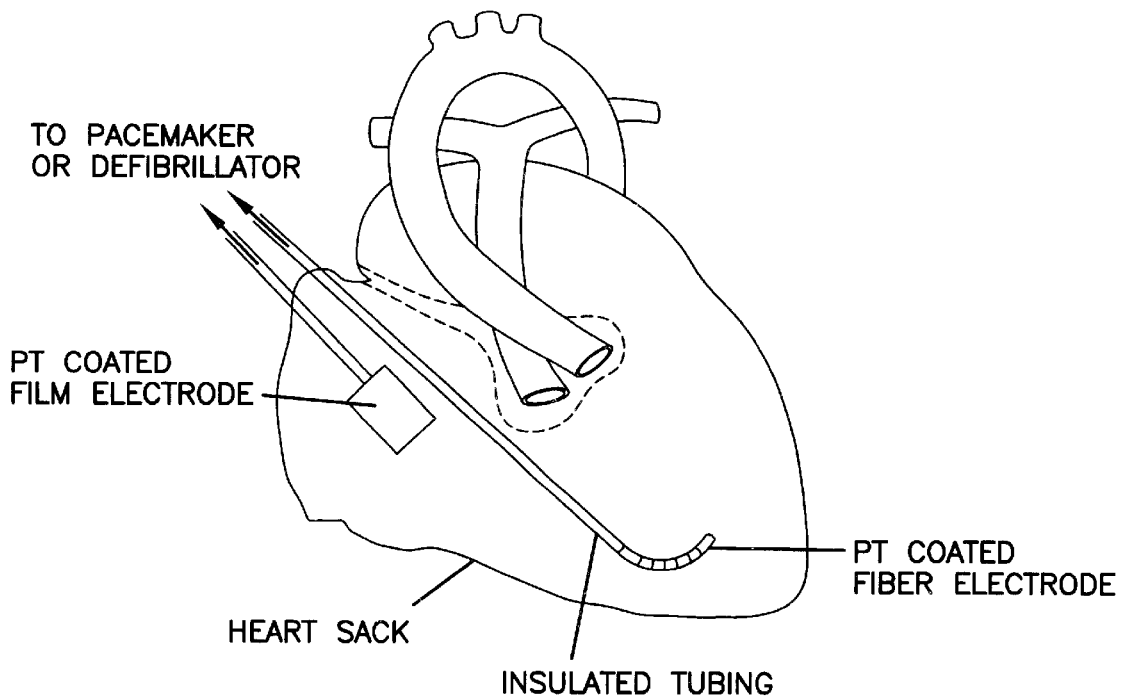
FIG.4 PERFORATED OR SEMIPERMEABLE HEARTSACK
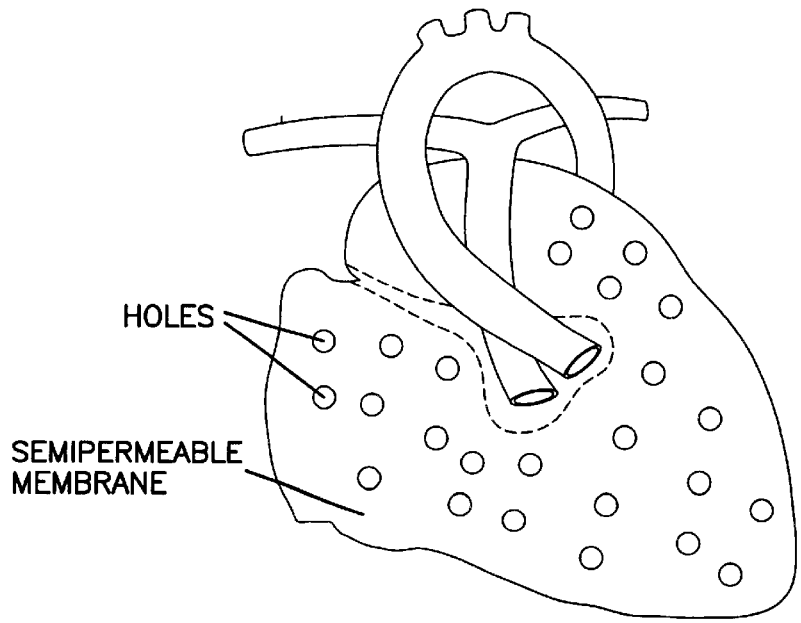

CARDIO THERAPEUTIC HEART SACK

This application claims the benefit of Prov. No. 60/106,960 filed Nov. 4, 1998

FIELD OF THE INVENTION

This invention relates to a biocompatible, biostable and implantable heart sack which is prepared from biocompatible, biostable and implantable elastomers selected from the group consisting of polyetherurethane, polycarbonateurethane, silicone, poly(siloxane) urethane and/or hydrogenated poly (styrene-butadiene) copolymer for the treatment of cardiomyopathy, hypertrophic cardiomyopathy, tachycardia, bradycardia, ventricular fibrillation, atrial fibrillation etc. The heart sack of this invention can be reinforced with mono-filaments, yarns, braids, cords, knitted or woven or non-woven cloth made of a biocompatible, biostable, implantable polyamide, polyimide, polyester, polypropylene, and/or polyurethane etc.

The heart sack of this invention can be equipped with pacemaker leads and defibrillation leads. The leads and electrodes of this invention are made of noble metal or stainless steel deposited, coated or plated mono-filaments, yarns, braids, cords, wires, films, cloth and/or cylindrical tubes. The noble metal used for this invention is selected from the group consisting of gold, platinum, rhodium and their alloys. The mono-filaments, yarns, braids, cords, wires, films, cloth or cylindrical tubes materials to be coated, deposited or plated with noble metal are selected from the group consisting of poly(ethylene terephthalate), poly (butylene terephthalate), polyamide, polyimide, polypropylene, polyetherurethane, polycarbonateurethane and their copolymers. The heart sack and electrodes are very flexible and have good biocompliance with heart muscle. They have high strength and excellent mechanical properties. Ordinary pacemaker leads and defibrillation leads could be also imbedded into the heart sack to provide cardiac pacing or defibrillation.

REFERENCE

| US4100309 | Jul. 11, 1977 | Micklus, et AL | 427/002.28 |
| US4515593 | May 7, 1985 | Norton; William J | 604/256 |
| US4573481 | Jun. 25, 1984 | Bullara; Leo A | 607/118 |
| US4612337 | Sep. 16, 1986 | Fox, Jr; Charles L | 514/038 |
| US4769013 | Jun. 4, 1986 | Lorenz et Al | 604/265 |
| US5242684 | Sep. 7, 1991 | Merianos; John J | 424/078.07 |
| US5324322 | Jun. 28, 1994 | Grill, et Al | 607/118 |

BACKGROUND OF THE INVENTION

Electrical therapeutic heart sack devices are a new and noble concept. Cardiomyopathy is a commonly observed disease in an aging population. Cardiomyopathy is a defect of myocardial function. There are three categories of Cardiomyopathies; dilated cardiomyopathy, hypertrophic cardiomyopathy and restrictive cardiomyopathy. Dilated cardiomyopathy refers to a condition in which there is weakened contraction of the ventricles with an apparent dilation of the ventricles. This leads to inadequate perfusion, and increased pulmonary and systemic venous congestion. It will lead essentially to loss of heart function. The history of the disease is one of progressive deterioration. The mortality in one year is greater than 50% for those people who have a poorly functioning heart. Hyper cardiomyopathy is a disease of the heart muscle. It is characterized with an overactive left ventricle due to its increase in muscle mass resulting in an obstruction of the blood that is being pumped from the left ventricle to the rest of the body. This causes dyspnea on exertion and chest pain due to ischemia. Currently, there is no treatment to alter the course of the disease. Restrictive cardiomyopathy is least common of cardiomyopathies. It is due to other pathological processes such as scerderma, amyloid, sarcoid, or storage decease. This invention is to prevent enlargement of the heart and thinning of the heart wall of patients with dilated cardiomyopathy, or hypertrophic cardiomyopathy by the use of a heart sack.

BRIEF SUMMARY OF THE INVENTION

The implantable heart sack of this invention was prepared from a biocompatible, biostable and implantable elastomer selected from the group consisting of polyetherurethane, polycarbonateurethane, silicone, polysiloxaneurethane and/or hydrogenated poly (styrene-butadiene) copolymer. Grooves can be made on the inside of the sack to accommodate blood vessels and pacing or defibrillation leads. Holes can be punched out from the heart sack to accommodate the pulmonary artery and aorta. The heart sack can be made to be a semipermeable membrane by providing numerous micro holes in the heart sack. This can be done mechanically, or by phase inversion casting method, or leaching out a soluble blend from an injection molded heart sack. Many larger holes can be perforated in the heart sack to allow body fluid to freely flow around the heart sack. The heart sack of this invention can be reinforced with mono-filaments, yarns, braids, cords, knitted, woven and/or non-woven cloth made of a biostable, implantable polyamide, polyimide, polyester, polypropylene, or polyurethane etc. The heart sack is split from the upper edge of the sack through the pulmonary artery and aorta openings. In this way, the sack can be opened to fit onto the heart. Several sutures are attached on one side or both sides of the cutting. Suturing makes the heart sack fit tightly onto the heart. Ordinary pacemaker leads and defibrillation leads can be imbedded into the heart sack to treat tachycardia, bradycardia, ventricular fibrillation, atrial fibrillation etc. However, the ordinary pacemaker leads that interface with the exterior of the heart often lack physical and physiological compliance with the heart muscle and its surrounding tissue resulting in mechanical abrasion and scar formation. To prevent abrasion, the pacemaker leads and/or electrode of this invention are made of noble metal or stainless steel coated, deposited or plated mono-filaments, yarns, braids, cords, wires, films, cloth cylindrical tubes, and laminated films. These articles are encased in multi-lumen insulating tubing having at least two lumens or in layers of the coaxial insulation tubes.

BRIEF DESCRIPTION OF THE FIGURES

FIG. 1 is an illustration of a heart showing some major blood vessels.

FIG. 2 is an illustration of a heart sac according to the invention.

FIG. 3 is an illustration of a heart sac in combination with fiber and film electrodes.

FIG. 4 is an illustration of a perforated or semipermeable heart sac according to the invention.

DETAILED DESCRIPTION OF THE INVENTION

When a man-made material is implanted in a human body, the body immediately recognizes the presence of the foreign material. This will trigger the immune defense system to eject or destroy the material and will cause edema, inflammation of the surrounding tissue, and biodegradation of the implanted material due to an enzymatic free radical attack, hydrolysis, oxidation and environmental stress cracking. Only a few polymers are known to possess a long term biostability, and good biocompatibility. The materials chosen for the implantable heart sack of this invention were selected from the group consisting of polyetherurethane, polycarbonateurethane, silicone, poly(siloxane) urethane, ethylene-propylene and dicyclopentadiene terpolymer, and/or hydrogenated poly (styrene-butadiene) copolymer. These polymers were chosen due to their elasticity, excellent biostability and biocompatibility. The heart sack can be prepared from casting, coating, extruding, molding of these biocompatible and biostable materials. The preferred polyurethane is selected from the group consisting of poly (tetramethylene-ether glycol) urethanes and poly (hexamethylenecarbonate-ethylenecarbonate glycol) urethanes such as Dow Chemical Company Pellethane™ 90A, and Pellethane™55D. The preferred polycarbonateurethane is Polymer Technology Inc Bionate™ or Thermedics Inc Carbothane™. The preferred silicone rubber has durometer hardness range of between 30 to 85. Both peroxide cure silicone and platinum cured silicone can be used. Examples are the Dow Coming Inc medical grade 70000 series, Q-4865 and Q-6860 series silicone, NuSil Inc MED 4535, 4550, 4560, 4750, 4770, and 4780 series silicone, and equivalent products of other manufacturers. The preferred polysiloxaneurethane is Elastomedics Elast-Eon™. The heart sack made from these polymers possesses excellent long-term biostability, good biocompatibility, no toxicity and good resistance to the environmental stress cracking. A heart sack can be reinforced with high strength fibers or filaments of polyamide, polyimide, polyester, and polypropylene or crosslinked polyurethane. The preferred reinforcing material is poly(ethylene terephthalate), and poly (butylene terephthalate). The filaments and cords prepared from these polymer have very high tensile strength and have good long-term biostability when imbedded in the aforementioned biocompatible and biostable elastomers. Contoured grooves can be made on the inside of the heart sack to accommodate blood vessels and pacing or defibrillation leads by designing dies for the casting or molding. The heart sack is split from the upper edge of the sack through the pulmonary artery, aorta and other blood vessel openings. In this way, the sack can be opened to fit onto the heart. Sutures are attached on one side or both sides of the cutting. Suturing enable to tie the heart sack tightly onto the heart.

The heart sack of this invention can be equipped with pacemaker leads and defibrillation leads. However, care must be taken to prevent mechanical abrasion of the heart muscle and surrounding tissues. Pacing and defibrillation leads of this invention comprises the noble metal coated, deposited, or plated mono-filaments, yarns, braids, cords, wires, films, cloth or cylindrical tubes, and laminated films that are encased in multi-lumen insulating sleeves or coaxial tubes. The metal coated, deposited or plated articles can be prepared by vacuum coating, vacuum deposition, chemical or physical deposition, spattering, chemical or electric reductions of the metallic ions or chemical plating etc. Noble metals such as gold, iridium, platinum, rhodium and their alloys or corrosion resistant stainless steel can be coated, deposited or plated onto fibers and films to form an electric conductive electrode and leads elements. Hereunder, these metal coated, deposited or plated products are referred as "noble metal coated" products.

To make the electrodes and leads, the noble metal coated mono-filaments, yarns, braids, cords, wires, films, cloth or cylindrical tubes, and laminated films etc. must have excellent electric conductivity, biostability and biocompatibility. Noble metals, which meet these requirements, due to their very low electric resistance, and excellent biostability and biocompatibility, are gold, platinum, rhodium and platinum-rhodium alloy. Preferred metals are platinum and platinum rhodium alloys. Platinum has an extremely low electric resistance of 0.000275 ohm per meter. Biostability, biocompatibility, and low electric resistance of platinum and platinum-rhodium alloys are extensively proven as the pacemaker and defibrillator electrodes.

The mono-filaments, yarns, braids, cords, wires, films, cloth or cylindrical tubes, and laminated films of this invention to be coated, deposited or plated with noble metal need to have high strength, good biocompatibility and long term biostability. Hereunder, these mono-filaments, yarns, braids, cords, wires, films, cloth or cylindrical tubes, and laminated films may be referred as "fiber and film" products. Polymers, which meet these requirements, are poly(ethylene terephthalate), poly(butylene terephthalate), polyamide, polyimide, polypropylene, polyurethane, and their copolymers. The preferred material to make fiber, filament yarn and film is poly(ethylene terephthalate) (PET). PET has an excellent physical strength, good biocompatibility, biostability, and is already utilized in construction of artificial heart valves, and artificial blood vessels.

The highly electric conductive noble metal coated articles described above are encased in multi-lumen insulating tubing having at least two lumens or encased in coaxial tubing. The elastomers, which have excellent insulating properties and which meet requirements for implantation are polyetherurethane, polycarbonateurethane, silicone, polysiloxaneurethane, polyfluoroethylene, or hydrogenated poly(styrene-butadiene) copolymer and the same as described in the above heart sack materials. Tubes made from these polymers are known to have an excellent long-term biostability, good biocompatibility, no toxicity and good resistance to the environmental stress cracking. It is known that hydrogen peroxide simulates the oxidative actions imposed by the body against an implanted foreign material. The use of hydrogen peroxide, or hydrogen peroxide plus cobalt chloride to test biostability of materials is described in Journal of Biomaterials Research Vol. 29, 467–475 and Journal of Biomedical Material Research Vol. 27, page 327–334.

A multi-lumen tube of at least three lumens is preferred for the bipolar leads. The coaxial leads can be fabricated from alternating layers of the aforementioned insulating tubing and an electrically conductive material made of the noble metal coated mono-filaments, yarns, braids, cords, wires, films, cloth or cylindrical tubes. A special alloy MP35N coil also can be used as the leads electric conductor. The leads are fabricated in such a way that one end of the leads or cable can be connected to a pacemaker or defibrillator. The noble metal coated fibers and/or films protrude from another end of the multi-lumen leads or coaxial leads for a designated length. They can be attached or bonded onto a narrow and thin strip of a insulating film, sheet or a sliced tube to form electrodes. The insulation material is made of one or more of the aforementioned biocompatible, biostable and implantable insulating polymer and has one or more grooves. The electrodes are bonded into grooves in parallel in a designated width, or the electrode is attached individually on the separate insulation material. Multiple grooves can be made to accommodate multiple electrodes. The insulation sheet that has grooves can be extruded using a film die with appropriate shape. To mount the noble metal coated fiber electrode into the groove, a round groove having the diameter slightly smaller to slightly larger than that of the fiber with $1/32$ to $1/2$ of the circumference opened or cut away is preferred. This enables the electrode to be retained in the grooves and leaves $1/32$ to $1/2$ of the metal-coated fiber surface exposed on the surface of the insulating sheet. In the same manner rectangular grooves can be made in an insulating sheet to accommodate the metal coated film electrodes. The noble metal coated films can be laminated with one or more of the aforementioned biocompatible, biostable and implantable elastomer sheet in parallel in a designated width from each other, or individually bonded onto the separate insulation material to make electrodes. The electrode and insulating ribbons can be heat treated and annealed to contour the heart sack. This assures tight contact with the heart muscle. The pacemaker leads are fabricated in such a way that one end of the leads can be connected to an implanted pacemaker or defibrillator. The noble metal coated electric conductive elements protruded from another end of the leads can be also connected to the regular pacemaker electrodes and defibrillator electrodes. When the MP35N coil or silver/MP35N coil is used as electric conductive material for the leads, a portion of the protruding MP35N coil can be connected to the ribbons or strips of metal coated fibers and bonded onto the insulation materials in the same manner described above. The connection area can be sealed with polyurethane, silicone or epoxy resin sealant to prevent short-circuiting and abrasion. The leads can be imbedded directly in the heart sack or inserted into the groove in the heart sack. The self-contouring and flexible electrodes provide excellent mechanical and physiological compliance to prevent mechanically induced damages such as thickened epineurium, increased subperineural and endoneural connective tissue, endoneural edima, demmyelinization, or axonal degeneration. An ordinary pacemaker leads and defibrillation leads can be also imbedded or inserted into the groove in the heart sack to treat tachycardia, bradycardia, ventricular fibrillation, atrial fibrillation etc. Similarly the ribbons or strips of the noble metal coated films that are laminated with the aforementioned implantable elastomer can be inserted or mounted onto separate areas of the inner side of the heart sack to provide for the proper pacing or defibrillation for the separate heart chamber. The film electrode, ribbon, fiber electrode and heart sack can be heated treated to shrink or form a contoured configuration to fit exactly onto the heart, so that the electrodes make tight contact with the heart wall.

The whole heart sack can be made semipermeable or totally permeable depending upon the hear sack size and physiological requirements. The semipermeable membrane can be prepared from a molding mixture of polymers with a designated molecular weight and proportion of leaching component. Pore size and porosity is proportional to the molecular weight and amount of leaching compound. Leaching out the soluble component from an injection molded heart sack creates a semipermeable membrane. A phase inversion casting method can be also used. Micro or macro holes can be also mechanically perforated in the heart sack. This will allow body fluid to freely flow around the heart sack. The number and size of holes can be optimized depend upon the size of heart sack and physiological requirements.

It is desirable to eliminate the friction among the heart sack, leads and heart muscle to prevent mechanically induced damage. The heart sack and noble metal coated leads materials have excellent biocompliance with the heart muscle. Further reduction in the coefficient of friction can be achieved by the use of a hydrophilic coating applied onto the leads and electrode insulation surface. The whole heart sack and leads assemblies, except the electrode surface, can be coated with a thin layer of a biocompatible, hydrophilic coating to lower coefficient of friction. This type of coating was prepared from the polyvinylpyrrolidone (PVP) polyurethane interpenetrating polymer. The coating solution was prepared from dissolving polyvinylpyrrolidone and urethane into organic solvents. A hydrophilic coating also can be made by depositing a solid polyvinylpyrrolidone derivative onto the heart sack. The PVP coating provides excellent biocompatibility and low coefficient of friction when wet with blood or body fluid. The coating swells in water but will not dissolve or leach out and is extremely hydrophilic.

An incidence of infection associated with the implantation of medical devices in the body is often life threatening. Some particularly persistent infectious organisms are staphylococcus, staphylococcus epidermis, and pseudomonas auerignosa. Staphylococcus is especially dangerous because it has an affinity for plastics. Entercoccus is another gram-positive organism that causes life-threatening infection and is resistant to a broad range of antibiotics. The incidence of infection associated with the implanted medical devices can be prevented with the use of antimicrobial agents. Coating, impregnation and compounding of antimicrobial agents on medical devices can prevent infection associated with the implant operation. Antimicrobial agents, which are suited for this purpose, are benzalkoniumchloride (BAC), chlorhexidine dihydrochloride (CHD), dodecarbonium chloride (DCC), and silver sufadiazine (SSD). The amount of antimicrobial agent required depends upon the agent. It generally ranges from 0.0001% to 0.5%. BAC, DCC and SSD can be dissolved or dispersed in coating. These antimicrobial agents can be added to the biocompatible, lubricious and hydrophilic coating described in above. Anti microbial agents can also be added to a bioresorbable polymer solution of polyglycolide, polylactide or collagen. Medical devices can then be coated with this antimicrobial solution. CHD due to its high decomposition temperature and good thermal stability can be compounded into polyurethane and silicone polymers and then extruded to form tubing, sheet and other shaped articles. These methods of antimicrobial coating, impregnation of the antimicrobial agents, or compounding of the antimicrobial agents into the insulation materials can be applied to any other type of heart sack, leads and electrodes.

EXAMPLE 1

A heart shaped polypropylene model including all blood vessel components was coated with a 10% solution of Pellethane 90AE in N-dimethylpyrrolidone and dried. The process was repeated three times to obtain an adequate coating thickness. Then, a screen made of poly(ethylene terephthalate) (PET) was placed onto the coated model and coated again with the Pellethane solution. Coating and drying were repeated several times. Then, the heart shaped skin was removed from the model by making a slit from the center upper edge to below the aorta to obtain a heart shaped sack. Then, a number of polypropylene sutures were attached on the both side of the slit. The sutures make it easier to close the slit and secure the heart sack on the heart.

EXAMPLE 2

A heart shaped polypropylene model including all blood vessel components was coated with a polyurethane solution prepared from polytetramethylene ether glycol having a molecular weight of 1,000, methylene bis-phenylisocyanate, and ethylenediamine in dimethylacetoamide and dried. The process was repeated two times to obtain an adequate coating thickness. Then, a screen made of poly(ethylene terephthalate) (PET) was placed onto the coated model and coated again with the Pellethane solution. Coating and drying were repeated several times. Then, the heart shaped skin was removed from the model by making a slit from the center upper edge to below the aorta to obtain a heart shaped sack. Then, a number of polypropylene sutures were attached on the both side of the slit. The sutures make it easier to close the slit and secure the heart sack on the heart.

EXAMPLE 3

To the Pellethane solution of example 1, two percent of polyethylene glycol having molecular weight of 1000 was dispersed. Then, the solution was applied to the polypropylene heart model in the same manner. The coating was dried and annealed. Thus obtained heart sack was placed in 60° C. water bath for 60 minutes to leach out the polyethylene glycol. After drying a heart sack with a semipermeable membrane was obtained.

EXAMPLE 4

Poly(ethylene terephthalate) monofilament having a 20 micron diameter was plated with approximately 0.5 micron thick platinum. A yarn consisting of 48 platinum deposited monofilament was braided to make an electrically conductive wire. The braid having a 60 mm length and 1.8 mm diameter had an electric resistance of 0.7 ohms. A platinum coated fiber braid 800 mm long and 0.6 mm in diameter had a tresistance of 35 ohms. The product had extremely good corrosion resistance. No corrosion was found after 400×15 amp 10 milli-second defibrillation shocks in 0.9% saline. The platinum-coated fiber had very low toxicity and passed both the ASTM F813 Cytotoxicity Assay and the Cell Growth Inhibition-Cytotoxicity Assay.

EXAMPLE 5

Two braids of platinum deposited poly(ethylene terephthalate) fibers having 0.6 mm dia were inserted into two lumen Pellethane tubing. The braids protruding from one end of the tubing were connected to the adapters that fit into a pacemaker. The braids protruding from the other end of the tube were bonded into a groove in the inner surface of the heart sack in such way that the electrodes are exposed on the inner surface of the heart sack. Then the heart sack was placed on the polypropylene heart model and annealed at 85° C. for two hours. After cooling hear sack equipped with the electrode and leads contoured with the heart sack was obtained.

EXAMPLE 6

MP 35N coils were placed in tubing (2.4 mm dia, 0.2 mm wall thickness) made of Pellethane 55D, Pellethane 80A, and peroxide cured silicone. Then, the tubing was bent in a U-shape and placed separately in 1-in diameter test tubes containing 10% peroxide solution. A braid made of platinum coated PET was also bent in the same u-shape and placed in a test tube containing 10% peroxide solution. Pellethane 55D which is manufactured by Dow Chemical and which is known as a biostable and biocompatible polyurethane and Pellethane 80A which is known to be susceptible to the environmental stress cracking under mechanical stress were used as positive and negative controls. Test tubes were covered by waxed plastic film and placed in an incubator at 37° C. After 6 weeks of incubation, the tubes and braids were examined under microscope. Micro-cracks were observed in the bent area of the Pellethane 80A tube. No cracks or fissures were observed on either the Pellethane 55D or the silicone and platinum coated PET.

EXAMPLE 7

Polytetramethylene ether urethane (PEU) was prepared from methylene diphenyl isocyanate (MDI), poly (tetramethylene ether) glycol (PEU), and butanediol. Films (2 mm×10 mm×0.5 mm) were extruded from the PEU. The same size films were also extruded from polycarbonateurethane (PCU) prepared from MDI and poly(hexamethylene carbonate-ethylene carbonate) glycol (PCU), and poly (ethylene terephthalate) (PET). Platinum coated poly (ethylene terephthalate) (Pt-PET) film, and PET film coated with polyvinylpyrrolidone interpolymer (Pt-PVP) were also obtained. All films were placed in separate vials and exposed to fresh platelet plasma concentrate. The vials were incubated at 37° C. for 30 minutes with slight agitation. Then, the films were rinsed in cold phosphate buffer and treated with 3% glutaraldehyde, dehydrated serially with increasing concentration of ethanol and air dried. Thus obtained samples were spatter coated with gold and examined using scanning electron microscope. The amounts of platelet adhesion and degree of platelet activation were measured. Round platelet and no pseudopodia present was rated 1, a few pseudopodia with no flattening was rated 2, one or more pseudopodia flattened and hyaloplasm not spread between pseudopodia was rated 3, hyaloplasm partially spread was rated 4 and hyaloplasm extensively spread were rated 5. Thus, the smaller the number the better the biocompatibility. The ratings obtained were: PEU 2, PET 4, PCU 3, Pt-PET 2, and Pt-PVP 1. PVP 1.

EXAMPLE 8

A semipermeable heart sack was obtained by coating and drying a heart shaped model with appropriate blood vessel features and have holes and grooves for the pacemaker leads or defibirillation leads or both, with a mixture of polyethylene glycol (PEG) having 600 molecular weight with the elastomer solution prepared from the reaction of polytetramethylene ether glycol having a molecular weight of 1,000 and methylene bis(p-phenylisocyanate) with the molar ratio of 1 to 1.6 to 1.9 respectively in N,N' dimethylacetoamide (DMA) at 85° C., then adding a mixture of ethylene diamine, 1,3 diaminocyclohexane and diethylamine in DMA (1:0.24:0.19 molar ratio respectively) to chain extend to obtaine approximately 30% solution, and adding 0.025% each of 4,4' buttylidene-bis (6-t-butyl m-cresol) and 2 diethyaminoethy methacrylate-n-decyl methacrylate copolymer as stabilizer. After a sufficient thickness is obtained by the repeated coating and drying processes, the product was placed in a 45° C. water bath to leach out the water soluble PEG. The porosity and pour size of the products were controlled by the molecular weight, amount of PEG and leaching temperature. Thus obtained heart sacks were removed from the mold making slits. Then, polypropylene sutures with needle were attached on both side of the slits. The suture enabled to secure the heart sack on the heart model and demonstrated convenience of the built-in suture.

EXAMPLE 9

The inner and outer surfaces of polyurethane heart sacks of example 8 were coated with a PVP urethane interpolymer solution. The coating solution was prepared dissolving 1.5 percent weight PVP having 30 Kvalue that is related to molecular weight of PVP, 0.5 percent weight of an adduct of methylene bis-cyclohexyl isocyanate and poly(tetraethylene ether) glycol having 1000 molecular weight, 0.3% isocyanate terminated caster oil and 0.005% stannous octoate catalyst in the mixture of solvents consisting of 35% methyl ethyl ketone, 20% ethyl lactate, 10% ethyl acetate, and 35% trichloroethylene. The coating was dried in an oven at 50° C. for 2 hours. A coated test sheet of polyurethane sheet prepared in the same manner demonstrated a high degree of lubricity when wet and had about one quarter the friction of Teflon.

EXAMPLE 10

A piece of polyvinylpyrrolidone-urethane coated heart sack material (2 cm diameter) was immersed in saline solutions containing 0.1% benzalkoniumchloride (BAC) and then dried. The pierce was placed on a culture dish containing staphylococcus epidermis and incubated at 37° C. for 3 days. A more than 5 mm of zone of inhibition was observed in the culture dish. Similarly, the polyvinylpyrrolidone-urethane coated electrodes immersed in saline solutions containing 0.1% of chlorhexidine dihydrochloride (CHD) and dodecarbonium chloride (DCC) showed more than 5 mm of zone of inhibition.

What the claims are:

1. A device for treating a disease of a heart, the device comprising:
    (a) biocompatible material configured to engage a surface of the heart to relieve tension on a wall of the heart;
    (b) one or more heat treated electrodes operably connected to the material and configured to contact a surface of the heart wherein the heat treated electrodes are heat treated to shrink to contour to the biocompatible material; and
    (c) a pacemaker operably connected to the electrodes.

2. The device according to claim 1, wherein the biocompatible material is elastic.

3. The device according to claim 1, wherein the biocompatible material comprises an elastomer selected from the group of polyetherurethane, polycarbonateurethane, silicone, poly(siloxane)urethane and hydrogenated poly(styrene-butadiene)copolymer.

4. The device according to claim 1, further comprising reinforcing fibers embedded in the biocompatible material.

5. The device according to claim 4, wherein the reinforcing fibers comprise a polymer selected from the group consisting of: polyamide, polyimide, polyester, polypropylene, poly urethane, and combinations thereof.

6. The device according to claim 4, wherein the reinforcing fibers comprise poly(ethylene terephthalate), poly(butylene terephthalate), or combinations thereof.

7. The device according to claim 4, wherein the device is in elastic.

8. The device according to claim 1, wherein the electrodes are encased in insulating tubing.

9. The device according to claim 8, wherein the insulating tubing comprises a material selected from the group consisting of: polyetherurethane, polycarbonateurethane, silicone, polysiloxaneurethane, polyfluoroethylene, hydrogenated poly(styrene-butadiene), and copolymers thereof.

10. The device according to claim 8, wherein the insulating tubing comprises multiple lumens to maintain the electrodes in electrical isolation.

11. The device according to claim 1, wherein the electrodes are imbedded in the biocompatible material.

12. The device according to claim 1, wherein the material defines holes.

13. A The device according to claim 1, wherein the material defines pores.

14. The device according to claim 1, wherein the material is semipermeable such that body fluid can freely flow around the device when in use.

15. The device according to claim 1, wherein the material is configured to surround the heart.

16. The device of claim 1, wherein the biocompatible material comprises silicone.

17. A device for treating a disease of a heart, the device comprising:
    (a) biocompatible material configured to engage a surface of the heart to relieve tension on a wall of the heart;
    (b) one or more heat treated electrodes operably connected to the material and configured to contact a surface of the heart, wherein the one or more electrodes are heat treated to shrink to contour to the biocompatible material;
    (c) a pacemaker operably connected to the electrodes; and
    (d) noble metal coating on the one or more electrodes.

18. The device of claim 17, wherein the noble metal coating coats at least one of the one or more electrodes.

19. A device for treating a disease of a heart, the device comprising:
    (a) biocompatible material configured to engage a surface of the heart to relieve tension on a wall of the heart;
    (b) one or more heat treated electrodes operably connected to the material and configured to contact a surface of the heart, wherein the one or more heat treated electrodes are heat treated to shrink to contour to the biocompatible material; and
    (c) a pacemaker operably connected to the electrodes,
    wherein the biocompatible material and the one or more electrodes are coated with a biocompatible coating.

20. The device of claim 19, wherein the biocompatible coating comprises a hydrophilic material.

* * * * *

UNITED STATES PATENT AND TRADEMARK OFFICE
CERTIFICATE OF CORRECTION

PATENT NO. : 6,587,734 B2
DATED : July 1, 2003
INVENTOR(S) : Okuzumi

It is certified that error appears in the above-identified patent and that said Letters Patent is hereby corrected as shown below:

Column 3,
Line 26, "Dow Coming Inc" should read -- Dow Corning Inc --

Column 10,
Line 2, "in elastic." should read -- inelastic. --
Line 17, "A The device" should read -- The device --

Signed and Sealed this

Twenty-third Day of September, 2003

JAMES E. ROGAN
*Director of the United States Patent and Trademark Office*